US012653671B2

(12) United States Patent
Costello et al.

(10) Patent No.: US 12,653,671 B2
(45) Date of Patent: Jun. 16, 2026

(54) DELIVERY SYSTEM HAVING A SPLIT DISTAL TIP FOR IMPROVED POSITIONING OF A TRANSCATHETER HEART VALVE

(71) Applicant: MEDTRONIC, INC., Minneapolis, MN (US)

(72) Inventors: Declan Costello, Mayo (IE); Edmond Sheahan, Galway (IE)

(73) Assignee: MEDTRONIC, INC., Minneapolis, MN (US)

( * ) Notice: Subject to any disclaimer, the term of this patent is extended or adjusted under 35 U.S.C. 154(b) by 805 days.

(21) Appl. No.: 17/999,129

(22) PCT Filed: May 27, 2021

(86) PCT No.: PCT/US2021/034421
§ 371 (c)(1),
(2) Date: Nov. 17, 2022

(87) PCT Pub. No.: WO2021/247351
PCT Pub. Date: Dec. 9, 2021

(65) Prior Publication Data
US 2023/0210660 A1     Jul. 6, 2023

Related U.S. Application Data

(60) Provisional application No. 63/034,555, filed on Jun. 4, 2020.

(51) Int. Cl.
*A61F 2/24* (2006.01)
*A61M 25/00* (2006.01)

(52) U.S. Cl.
CPC ....... *A61F 2/2436* (2013.01); *A61M 25/0074* (2013.01); *A61M 25/0069* (2013.01)

(58) Field of Classification Search
CPC ............ A61F 2002/9534; A61F 2/9517; A61F 2/962; A61F 2/966; A61F 2/2436;
(Continued)

(56) References Cited

U.S. PATENT DOCUMENTS 7,914,569 B2   3/2011  Nguyen et al.
8,702,780 B2   4/2014  Hartley et al.
(Continued)

OTHER PUBLICATIONS

International Search Report issued Sep. 14, 2021 in Intl Appl. No. PCT/US2021/034421.

*Primary Examiner* — Sarah W Aleman
*Assistant Examiner* — Paris Marie Blass
(74) *Attorney, Agent, or Firm* — MEDLER FERRO WOODHOUSE & MILLS PLLC

(57)               ABSTRACT

A delivery system includes a handle, an inner shaft having a distal portion configured to receive the heart valve prosthesis thereon, a push wire slidingly disposed through a lumen of the inner shaft, and an outer sheath configured to cover the heart valve prosthesis during delivery. A split distal tip or nosecone is attached to a distal end of the inner shaft and includes at least one cutout portion formed through a sidewall thereof. A proximal end of the push wire is operatively coupled to an actuator of the handle and a distal end of the push wire is attached to the cutout portion of the nosecone. When the nosecone is in a delivery configuration the cutout portion is substantially flush with the sidewall of the nosecone. When the nosecone is in a deployed configuration the cutout portion is spaced apart from the sidewall of the nosecone.

13 Claims, 10 Drawing Sheets

(58) Field of Classification Search
CPC .......... A61F 2/95; A61F 2/2427; A61F 2/958;
A61F 2002/9665; A61M 25/002; A61M
25/0067; A61M 25/0069; A61M 25/0074;
A61M 25/0147; A61M 25/0133; A61M
2025/09125; A61M 2025/09116; A61B
17/12122
See application file for complete search history.

(56) References Cited

U.S. PATENT DOCUMENTS

| | | | |
|---|---|---|---|
| 9,381,083 B2 | 7/2016 | Costello | |
| 10,478,297 B2 | 11/2019 | Ahlberg et al. | |
| 2008/0255652 A1* | 10/2008 | Thomas | A61F 2/95 623/1.2 |
| 2012/0035722 A1 | 2/2012 | Tuval | |
| 2012/0301572 A1 | 11/2012 | Barnes | |
| 2017/0361062 A1 | 12/2017 | Syed | |
| 2019/0060068 A1 | 2/2019 | Cope et al. | |
| 2019/0254816 A1* | 8/2019 | Anderson | A61F 2/2418 |

* cited by examiner

301

304

306

302

307

301

306

308

DELIVERY SYSTEM HAVING A SPLIT DISTAL TIP FOR IMPROVED POSITIONING OF A TRANSCATHETER HEART VALVE

FIELD OF THE INVENTION

The present invention is related to delivery systems for and methods of delivering self-expanding prostheses.

BACKGROUND

Flexible prosthetic valves supported by stent structures that can be delivered percutaneously using a catheter-based delivery system have been developed for heart and venous valve replacement. These prosthetic valves may include either self-expanding, balloon-expandable, or mechanically expandable stent structures with valve leaflets attached to the interior of the stent structure. The prosthetic valve can be reduced in diameter, mechanically onto a delivery catheter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place.

In general, rather than performing an open surgical procedure that may be traumatic and invasive, prostheses are preferably deployed through a less invasive intraluminal delivery procedure. More particularly, a lumen or vasculature is accessed percutaneously at a convenient and less traumatic entry point, and the prosthesis is routed through the vasculature to the site where the prosthesis is to be deployed. Intraluminal deployment is typically affected using a delivery catheter with coaxial inner and outer tubes arranged for relative axial movement. For example, a self-expanding valve prosthesis may be compressed and disposed within the distal end of an outer tube or sheath of the delivery catheter. The delivery catheter is then maneuvered, typically routed through a body lumen until the end of the delivery catheter and the prosthesis are positioned at the intended treatment site. The inner tube or shaft is then held stationary while the outer tube or sheath of the delivery catheter is withdrawn. A stop may be utilized to prevent the prosthesis from being withdrawn with the outer tube or sheath. As the outer tube or sheath is withdrawn, the prosthesis is released from the confines of the outer tube or sheath and radially self-expands so that at least a portion of the prosthesis contacts and substantially conforms to a portion of the surrounding interior of the lumen, e.g., the blood vessel wall, anatomical conduit, and/or cardiac anatomy.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the heart valve prosthesis, conduction disturbances, coronary artery obstruction, and/or undesirable paravalvular leakage and/or regurgitation at the implantation site. More particularly, for example, a prosthesis that is positioned too deep relative to the native annulus or placed unevenly within the native annulus in terms of depth may cause conduction disturbances. In another example, if a prosthesis is not circumferentially centered relative to the native annulus, the deployed prosthesis may dislodge from the implantation site and/or undesirable paravalvular leakage and/or regurgitation may occur. Thus, it is imperative that the prosthesis be accurately located relative to the native annulus prior to full deployment of the prosthesis.

Embodiments hereof are directed to a delivery system for a transcatheter valve prosthesis for positioning a valve prosthesis in situ with improved accuracy to address one or more of the aforementioned complications.

SUMMARY

Embodiments hereof relate to a delivery system for percutaneously delivering a valve prosthesis to a native heart valve includes a handle having at least one actuator thereon, an inner shaft having a distal portion configured to receive the heart valve prosthesis thereon, and at least one push wire. The inner shaft defines at least one lumen therethrough and the at least one push wire is slidingly disposed through the at least one lumen of the inner shaft. A nosecone is attached to a distal end of the inner shaft, and includes at least one cutout portion formed through a sidewall thereof. A proximal end of the at least one push wire is operatively coupled to the at least one actuator of the handle and a distal end of the at least one push wire is attached to the at least one cutout portion of the nosecone. When the nosecone is in a delivery configuration the at least one cutout portion is substantially flush with the sidewall of the nosecone. When the nosecone is in a deployed configuration the at least one cutout portion is spaced apart from the sidewall of the nosecone.

Embodiments hereof also relate to a method of positioning a valve prosthesis in a native heart valve. The heart valve prosthesis mounted on a delivery system is advanced to the native heart valve through the vasculature. The delivery system includes an inner shaft defining at least one lumen therethrough and including a nosecone attached to a distal end thereof. The nosecone includes at least one cutout portion formed through a sidewall thereof. At least one push wire is slidingly disposed through the at least one lumen of the inner shaft, a distal end of the at least one push wire being attached to the at least one cutout portion of the nosecone. The nosecone is in a delivery configuration in which the at least one cutout portion is substantially flush with the sidewall of the nosecone during the step of advancing the heart valve prosthesis and the heart valve prosthesis is in a delivery configuration during the step of advancing the heart valve prosthesis. The heart valve prosthesis is positioned within the native heart valve. The nosecone is deployed to a deployed configuration in which the at least one cutout portion is spaced apart from the sidewall of the nosecone by longitudinally advancing the at least one push wire. The at least one cutout portion is moved into contact with anatomy of the native heart valve. The at least one cutout portion pushes again the anatomy of the native heart valve to deflect the heart valve prosthesis and thereby radially center the heart valve prosthesis within the native heart valve.

BRIEF DESCRIPTION OF THE DRAWINGS

The accompanying figures, which are incorporated herein, form part of the specification and illustrate embodiments of a delivery system. Together with the description, the figures further explain the principles of and enable a person skilled in the relevant art(s) to make, use, and implant the prosthesis described herein. In the drawings, like reference numbers indicate identical or functionally similar elements.

DETAILED DESCRIPTION OF THE INVENTION

Figures 1, 1A, 1B:
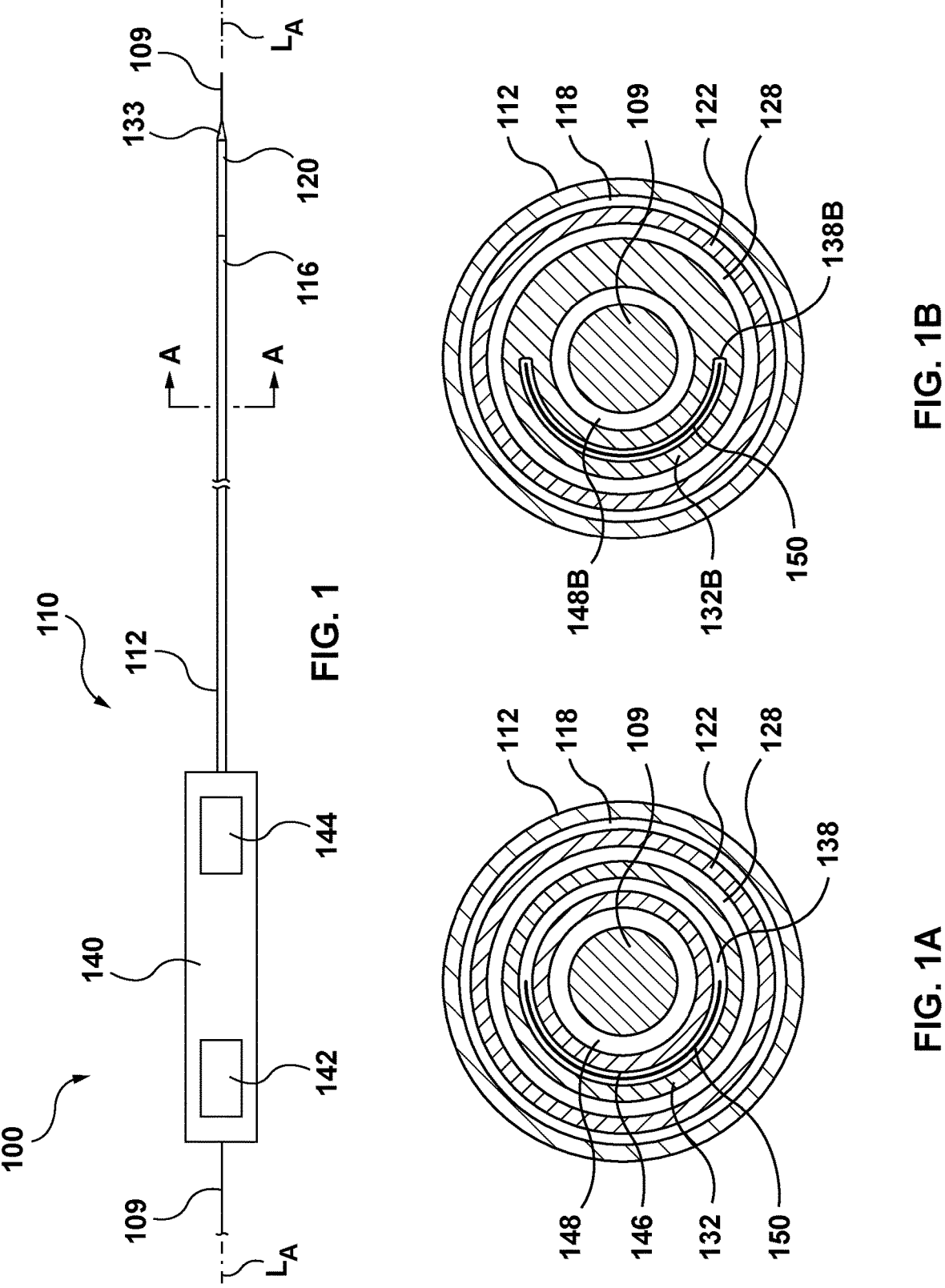
FIG. 1 is a side view of a delivery system according to an embodiment hereof, wherein the delivery system is in a delivery configuration in which a heart valve prosthesis is in a radially compressed configuration and a nosecone of the delivery system is in a delivery configuration.
FIG. 1A is a cross-sectional view of the delivery system of FIG. 1 taken along line A-A of FIG. 1.
FIG. 1B is a cross-sectional view of a delivery system according to another embodiment hereof taken along line A-A of FIG. 1.

Specific embodiments of the present invention are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the prosthesis "proximal" is the upstream portion or direction of blood flow when the prosthesis is deployed while "distal" is the downstream portion or direction of blood flow when the prosthesis is deployed. In addition, the term "self-expanding" is used in the following description with reference to one or more stent structures of the prostheses hereof and is intended to convey that the structures are shaped or formed from a material that can be provided with a mechanical memory to return the structure from a radially compressed or constricted delivery configuration to a radially expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely illustrative in nature and is not intended to limit the invention or the application and uses of the invention. Although the description of embodiments hereof are in the context of delivery systems for delivering a heart valve prosthesis within a native aortic valve, the delivery systems of the invention can also be used in other areas of the body, such as for delivering a heart valve prosthesis within a native mitral valve, for delivering a heart valve prosthesis within a native pulmonic valve, for delivering a heart valve prosthesis within a native tricuspid valve, for delivering a venous valve, or for delivering a heart valve prosthesis within a previously-implanted prosthesis. Furthermore, there is no intention to be bound by any expressed or implied theory presented in the preceding technical field, background, brief summary or the following detailed description.

Embodiments hereof relate to a delivery system for percutaneously delivering a heart valve prosthesis with improved positioning accuracy. The delivery system includes a nosecone having at least one cutout portion formed through a sidewall thereof. When the nosecone is in a delivery configuration the cutout portion is substantially flush with the sidewall of the nosecone. When the nosecone is in a deployed configuration the cutout portion is spaced apart from the sidewall of the nosecone and may be advanced to contact or push against a wall of the heart, for example, a ventricle wall such as the interventricular septum, or an atrial wall such as the interatrial septum, to accurately position or center the heart valve prosthesis within the native valve annulus.

Figure 1C:
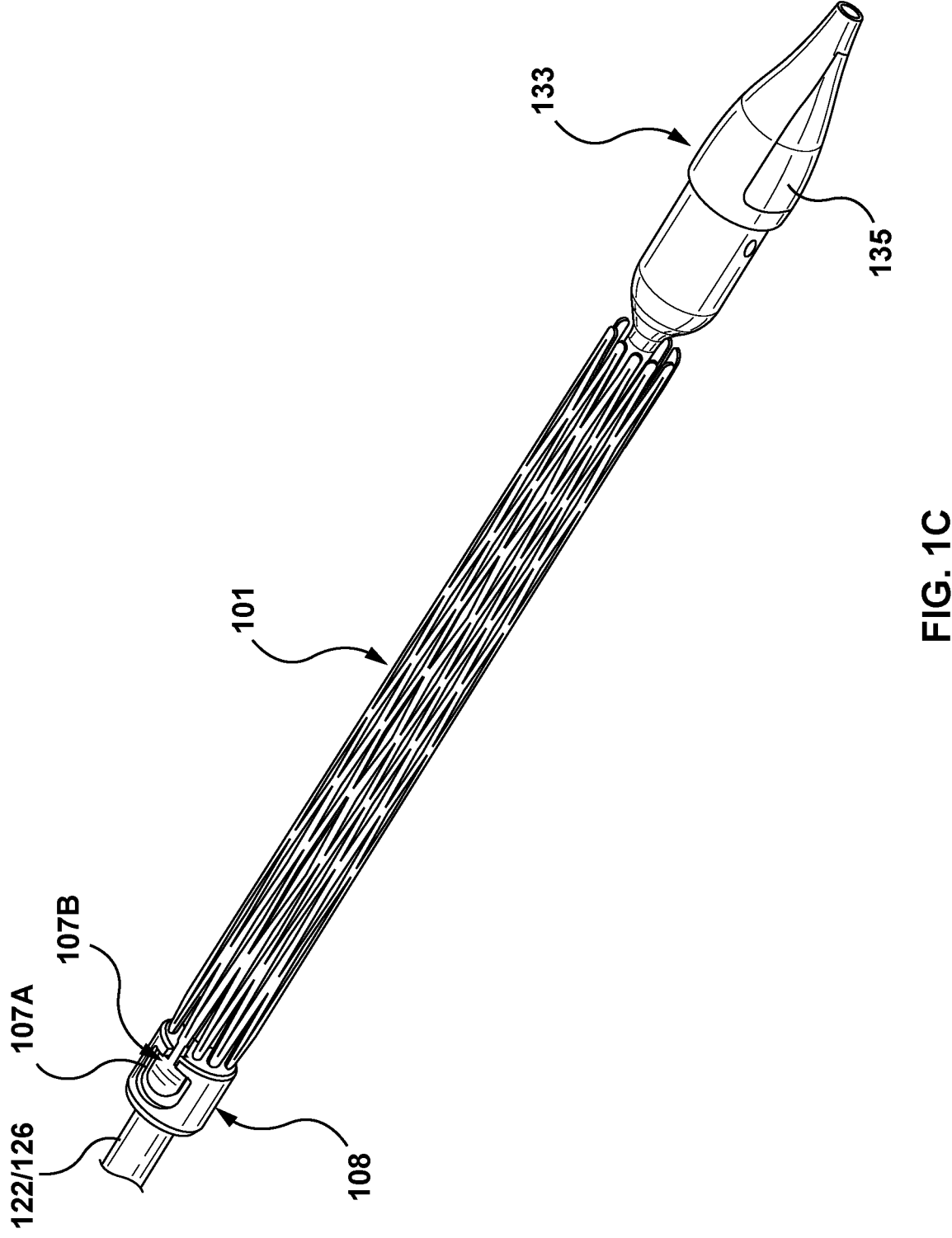
FIG. 1C is a perspective view of a distal portion of the delivery system of FIG. 1, wherein the delivery system is in the delivery configuration and an outer sheath of the delivery system is not shown for illustrative purposes only.
Figure 2:
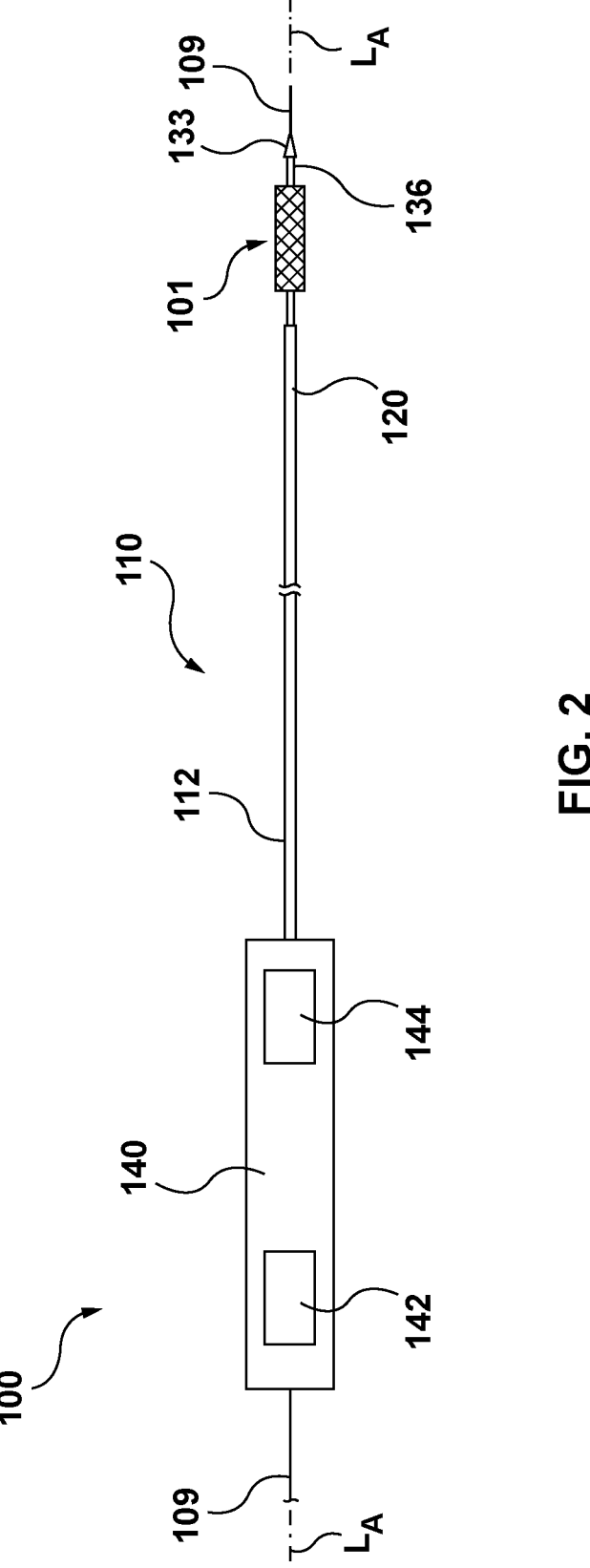
FIG. 2 is a side view of the delivery system of FIG. 1, wherein the heart valve prosthesis is in a radially expanded configuration and the nosecone of the delivery system is in the delivery configuration.

The delivery system will be described in more detail with reference to the figures. A delivery system 100 includes a heart valve prosthesis 101 and a delivery device 110 configured to percutaneously deliver the heart valve prosthesis 101 with improved positioning accuracy. More particularly, the delivery system 100 is shown in FIGS. 1, 1A, 1C, and 2. FIG. 1 is a side view of the delivery system 100, with an optional outer sheath 112 thereof surrounding the heart valve prosthesis 101 (not shown in FIG. 1). For a self-expanding heart valve prosthesis, the outer sheath can surround and constrain the prosthesis. For a mechanically expandable or balloon expandable heart valve prosthesis, the outer sheath, if present, can surround without constraining the prosthesis. A delivery device configured to deliver a mechanically expandable prosthesis or a balloon expandable prosthesis does not require an outer sheath. In FIG. 1, the delivery system 100 is in a delivery configuration in which the heart valve prosthesis 101 (not shown in FIG. 1) is in a radially crimped, compressed or collapsed configuration within the outer sheath 112 and a split distal tip or nosecone 133 of the delivery system 100 is in a delivery configuration. FIG. 1A is a cross-sectional view taken along line A-A of FIG. 1A. FIG. 1C is a perspective view of a distal portion of the delivery system 100 in the delivery configuration with the outer sheath 112 not shown. FIG. 2 is a side view of the delivery system 100 after an outer sheath 112 has been retracted to allow a self-expanding prosthesis 101 to be deployed, for example, to self-expand to a deployed or expanded configuration. For a balloon or mechanically expandable prosthesis 101 the prosthesis is mechanically or balloon expanded to a deployed configuration. The delivery device 110 includes a handle 140 having a first actuator 142 for manipulating a push wire 150 as will be explained in more detail herein and an optional second actuator 144 for manipulating the optional outer sheath 112 as will be explained in more detail herein. The handle 140 can have any shape or size appropriate for convenient handling by a user.

In addition to an optional outer sheath 112 operatively coupled to the handle 140, the delivery device 110 includes a shaft for retaining the heart valve prosthesis 101. In some embodiments, a distal end portion of the prosthesis retaining shaft includes a prosthesis retention member which is releasably coupled to the heart valve prosthesis 101. In some embodiments, a distal end portion of the shaft includes a balloon for expanding a balloon expandable prosthesis. In some embodiments, the distal end of the prosthesis retaining shaft is attached or coupled to a split distal tip or nosecone as described herein. If present, the outer sheath can define a lumen and is slidingly and concentrically disposed over the prosthesis retaining shaft. In some embodiments, the split distal tip or nosecone is attached or coupled to a second shaft and the prosthesis 101 is retained by or coupled to a first shaft, wherein the first or middle shaft can define a lumen and is concentrically disposed over the second or inner shaft.

In one embodiment, the delivery device 110 includes an outer sheath 112 operatively coupled to the handle 140, a middle shaft 122 disposed within the outer sheath 112, and an inner shaft 132 disposed within the middle shaft 122. The outer sheath 112, the middle shaft 122, and the inner shaft 132 each distally extend from within the handle 140.

The outer sheath 112 has a proximal end (not shown) disposed within the handle 140 and a distal end 116. As best shown in FIG. 1A, the outer sheath 112 defines a lumen 118 and is slidingly and concentrically disposed over the middle shaft 122. As used herein, "slidably" denotes back and forth movement in a longitudinal direction along or generally parallel to a central longitudinal axis LA of the delivery system 100. A distal portion of the outer sheath 112 defines a capsule 120. The capsule 120 is configured to retain the heart valve prosthesis 101 in a collapsed configuration for delivery to the desired treatment location. While the capsule 120 is described herein as a distal portion of the outer sheath 112, the capsule 120 may be a separate component coupled to the distal end of the outer sheath 112. Moreover, although the outer sheath 112 is described herein as a single component, this is not meant to limit the design, and the outer sheath 112 may include components such as, but not limited to a proximal shaft or other components suitable for the purposes described herein.

The second actuator 144 of the handle 140 is configured for retracting the capsule 120. The second actuator 144 is coupled to the outer sheath 112, and is generally constructed to provide selective proximal retraction and distal advancement of the outer sheath 112, and particularly of the capsule 120 attached thereto, relative to the heart valve prosthesis 101 held in a radially compressed, delivery configuration therein for covering and uncovering the heart valve prosthesis 101. The second actuator 144 may assume any construction that is capable of providing the desired sheath actuation functionality, such as those described in U.S. Pat. No. 8,579,963 to Tabor, which is assigned to the same assignee as the present disclosure and which is herein incorporated by reference in its entirety.

The middle shaft 122 is slidingly disposed between the outer sheath 112 and the inner shaft 132. The middle shaft 122 has a proximal end (not shown) disposed within the handle 140 and a distal end 126 disposed inside of the outer sheath 112 when the outer sheath 112 is disposed over the heart valve prosthesis 101. The distal end 126 of the middle shaft 122 includes a prosthesis retention member or spindle 108 which is releasably coupled to an end of the heart valve prosthesis 101. As best shown on the perspective view of FIG. 1C, having the outer sheath 112 removed for illustrative purposes only, the spindle 108 is a tubular component having at least one recess 107A formed on an outer surface thereof that is configured to receive a paddle 107B extending proximally from the heart valve prosthesis 101. The paddle 107B fits within or mates with the recess 107A of the spindle 108. Although only one recess 107A is visible on FIG. 1B, it will be understood by one of ordinary skill in the art that the spindle 108 may include two or more recesses for receiving a mating paddle of the heart valve prosthesis 101, such as for example first and second recesses at opposing locations on the spindle 108. As best shown in FIG. 1A, the middle shaft 122 defines a lumen 128 and is concentrically disposed over the inner shaft 132. Further, in embodiments, the middle shaft 122 terminates at the spindle 108.

The inner shaft 132 has a proximal end (not shown) which terminates within the handle 140 and a distal end 136. The nosecone 133 is coupled to the distal end 136 of the inner shaft 132 as shown in FIG. 1 and FIG. 2. As best shown in FIG. 1A which is a cross-sectional view of the delivery system 100 taken along line A-A of FIG. 1, the inner shaft 132 defines a lumen 138 and is concentrically disposed over a guidewire shaft 146. The guidewire shaft 146 defines a lumen 148 such that the delivery system 100 may be slidingly disposed and tracked over a guidewire 109. The push wire 150 is slidingly disposed within the lumen 138 of the inner shaft 132. Stated another way, the push wire 150 is slidingly disposed within the annular space defined between an inner surface of the inner shaft 132 and an outer surface of the guidewire shaft 146. In another embodiment hereof, the guidewire shaft 146 may be omitted and the inner shaft may alternatively be constructed as a dual lumen shaft formed for example by multi-lumen profile extrusion. More particularly, as shown in FIG. 1B which is a cross-sectional view of a delivery system according to another embodiment hereof taken along line A-A of FIG. 1, an inner shaft 132B defines a first or C-shaped lumen 138B which is pre-formed in the wall of the inner shaft 132B and is configured to slidingly receive the push wire 150 having a C-shaped cross-section. The inner shaft 132B also defines a second or guidewire lumen 148B configured to slidingly receive the guidewire 109. In another embodiment (not shown), the first or C-shaped lumen 138B as well as the push wire 150 disposed there-through may have different configurations or shapes including oval or circular.

A proximal end (not shown) of the push wire 150 is operatively coupled to the first actuator 142 of the handle 140 and a distal end of the push wire 150 is attached to a cutout portion 135 of the nosecone 133. In an embodiment, the push wire 150 is formed from Nitinol or stainless steel and the distal end of the push wire 150 is attached to the cutout portion 135 of the nosecone 133 using a weld, bonding or adhesive. As will be described in more detail herein with respect to FIGS. 5-6, the cutout portion 135 of the nosecone 133 may be distally advanced from the remainder of the nosecone 133 in order to contact and push against the anatomy, thereby deflecting and radially centering the heart valve prosthesis 101 disposed within the capsule 120 within the native heart valve. While the push wire 150 is primarily housed or disposed within the lumen 138 of the inner shaft 132, the proximal end thereof is accessible via the handle 140 to be pulled or pushed which results in controlled longitudinal movement of the cutout portion 135 of the nosecone 133. More particularly, the first actuator 142 of the handle 140 is configured to longitudinally move the push wire 150 within the lumen 138 of the inner shaft 132. The first actuator 142 is generally constructed to provide selective proximal retraction and distal advancement of the push wire 150, and particularly of the cutout portion 135 of the nosecone 133 attached thereto. The first actuator 142 may assume any construction that is capable of providing the desired push wire actuation functionality, such as those described in U.S. Pat. No. 10,278,852 to Griffin, which is assigned to the same assignee as the present disclosure and which is herein incorporated by reference in its entirety.

The inner shaft 132 is configured to receive the heart valve prosthesis 101 on a distal portion thereof and the outer sheath 112 is configured to compressively retain the heart valve prosthesis 101 on the distal portion of the inner shaft 132 during delivery, as shown in FIG. 1. Stated another way, the outer sheath 112 surrounds and constrains the heart valve prosthesis 101 in a radially compressed or delivery configuration. As previously described, the distal end 126 of the middle shaft 122 includes the spindle 108 to which the heart valve prosthesis 101 is releasably coupled. The heart valve prosthesis 101 is shown in the view of FIG. 2 but is obscured from view by the outer sheath 112 in FIG. 1. During deployment of the heart valve prosthesis 101 in situ, the outer sheath 112 is proximally retracted with respect to the heart valve prostheses 101, thereby incrementally exposing the heart valve prosthesis 101 until the self-expanding heart valve prosthesis 101 is fully exposed and thereby released from the delivery device 110. The middle shaft 122, the inner shaft 132 and the heart valve prosthesis 101 are held stationary while the outer sheath 112 is proximally retracted. When the outer sheath 112 is proximally retracted beyond the spindle 108, the paddles 107B of the heart valve prosthesis 101 are no longer held within the recesses 107A of the spindle and the heart valve prosthesis 101 is permitted to fully self-expand to its deployed configuration.

Figures 3, 4:
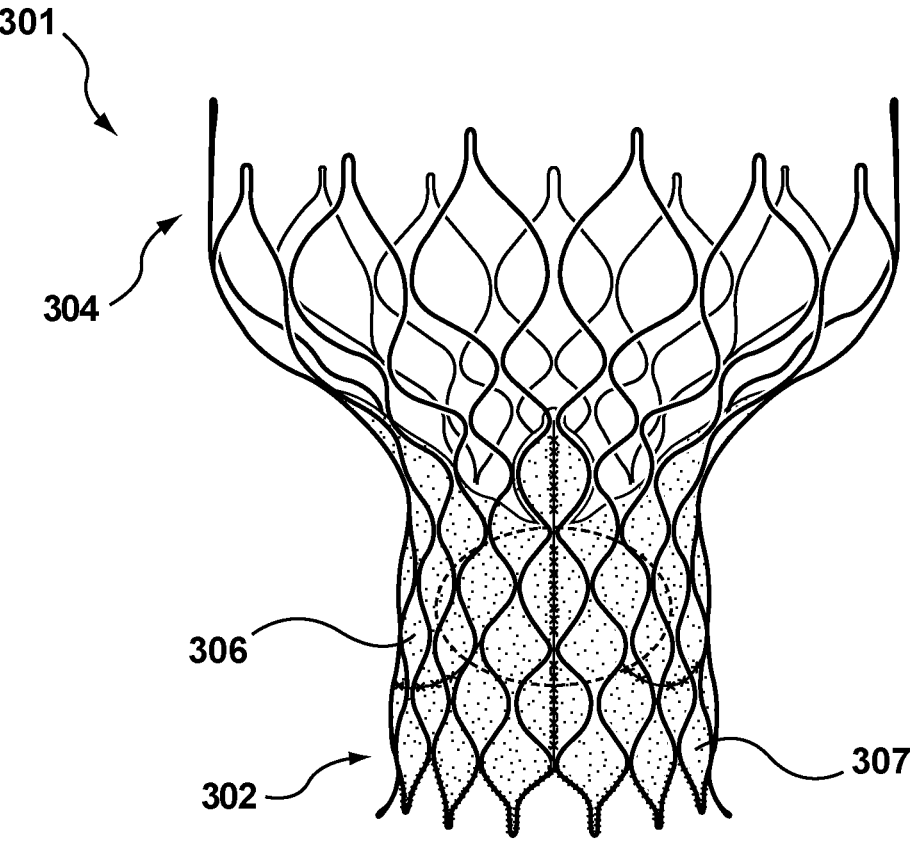
FIG. 3 is a side perspective view of a heart valve prostheses for use in embodiments hereof.
FIG. 4 is an end view of the heart valve prosthesis of FIG. 3.

FIG. 3 and FIG. 4 illustrate side perspective and end views, respectively, of a heart valve prosthesis 301 that may be utilized as the heart valve prosthesis 101 according to an embodiment hereof. The heart valve prosthesis 301 is merely exemplary and is described in more detail in U.S. Pat. No. 7,914,569 to Nguyen et al., which is herein incorporated by reference in its entirety. It is understood that any number of alternate heart valve prostheses can be used with the delivery devices and methods described herein. In addition, the delivery device 110 may also be used with other self-expanding prostheses such as stent-graft prostheses, uncovered stents, bare metal stents, drug eluting stents, and any self-expanding structure that is configured to fore-shorten during deployment.

The heart valve prosthesis 301 includes an expandable stent or frame 306 that supports a prosthetic valve component 308 within the interior of the frame 306. In embodiments hereof, the frame 306 is self-expanding to return to an expanded state from a compressed or constricted delivery state. In the embodiment depicted in FIGS. 3 and 4, the frame 306 has an expanded, longitudinally asymmetric hourglass configuration including a first end or portion 302 and a relatively enlarged second end or portion 304. Each portion of the frame 306 may be designed with a number of different configurations and sizes to meet the different requirements of the location in which it may be implanted. When configured as a replacement for an aortic valve, as shown for example in FIGS. 15-17 described in more detail herein, the first end 302 functions as an inflow end of the heart valve prosthesis 301 and extends into and anchors within the aortic annulus of a patient's left ventricle, while the enlarged second end 304 functions as an outflow end of the heart valve prosthesis 301 and is positioned in the patient's ascending aorta. When configured as a replacement for a mitral valve, the enlarged second end 304 functions as an inflow end of the heart valve prosthesis 301 and is positioned in the patient's left atrium, while the first end 302 functions as an outflow end of the heart valve prosthesis 301 and extends into and anchors within the mitral annulus of a patient's left ventricle. For example, U.S. Patent Application Publication Nos. 2012/0301572 to Kovalsky et al. and 2012/0035722 to Tuval, each of which are herein incorporated by reference in their entirety, illustrate heart valve prostheses configured for placement in a mitral valve. Each portion of the frame 306 may have the same or different cross-portion which may be for example circular, ellipsoidal, rectangular, hexagonal, rectangular, square, or other polygonal shape, although at present it is believed that circular or ellipsoidal may be preferable when the heart valve prosthesis is being provided for replacement of the aortic or mitral valve. As alternatives to the deployed asymmetric hourglass configuration of FIGS. 3 and 4, the frame 306 may have a symmetric hourglass configuration, a generally tubular configuration, or other stent configuration or shape known in the art for valve replacement.

As previously mentioned, the heart valve prosthesis 301 includes the prosthetic valve component 308 within the interior of frame 306. The prosthetic valve component 308 is capable of blocking flow in one direction to regulate flow there through via valve leaflets that may form a bicuspid or tricuspid replacement valve. FIG. 4 is an end view of FIG. 3 and illustrates an exemplary tricuspid valve having three leaflets, although a bicuspid leaflet configuration may alternatively be used in embodiments hereof. More particularly, if the heart valve prosthesis 301 is configured for placement within a native valve having three leaflets such as the aortic, tricuspid, or pulmonary valves, the heart valve prosthesis 301 may include three valve leaflets. If the heart valve prosthesis 301 is configured for placement within a native valve having two leaflets such as the mitral valve, the heart valve prosthesis 301 may include two valve leaflets. However, this is not meant to be limiting, and if the heart valve prosthesis 301 is configured to placement within a native valve having three leaflets or two leaflets, the heart valve prosthesis 301 may include the prosthetic valve component 308 having two leaflets, three leaflets, four leaflets, or any number of leaflets deemed suitable for the particular situation. Valve leaflets are sutured or otherwise securely and sealingly attached to the interior surface of the frame 306 and/or graft material 307 which encloses or lines the frame 306 as would be known to one of ordinary skill in the art of prosthetic tissue valve construction. Leaflets are attached along their bases to the graft material 307, for example, using sutures or a suitable biocompatible adhesive. Adjoining pairs of leaflets are attached to one another at their lateral ends to form commissures. The orientation of the leaflets within the frame 306 would change depending on which end of the heart valve prosthesis 301 is the inflow end and which end of the heart valve prosthesis 301 is the outflow end, thereby ensuring one-way flow of blood through the heart valve prosthesis 301.

Leaflets may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

The graft material 307 may also be a natural or biological material such as pericardium or another membranous tissue such as intestinal submucosa. Alternatively, the graft material 307 may be a low-porosity woven fabric, such as polyester, Dacron fabric, or PTFE, which creates a one-way fluid passage when attached to the stent. In one embodiment, the graft material 307 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 5:
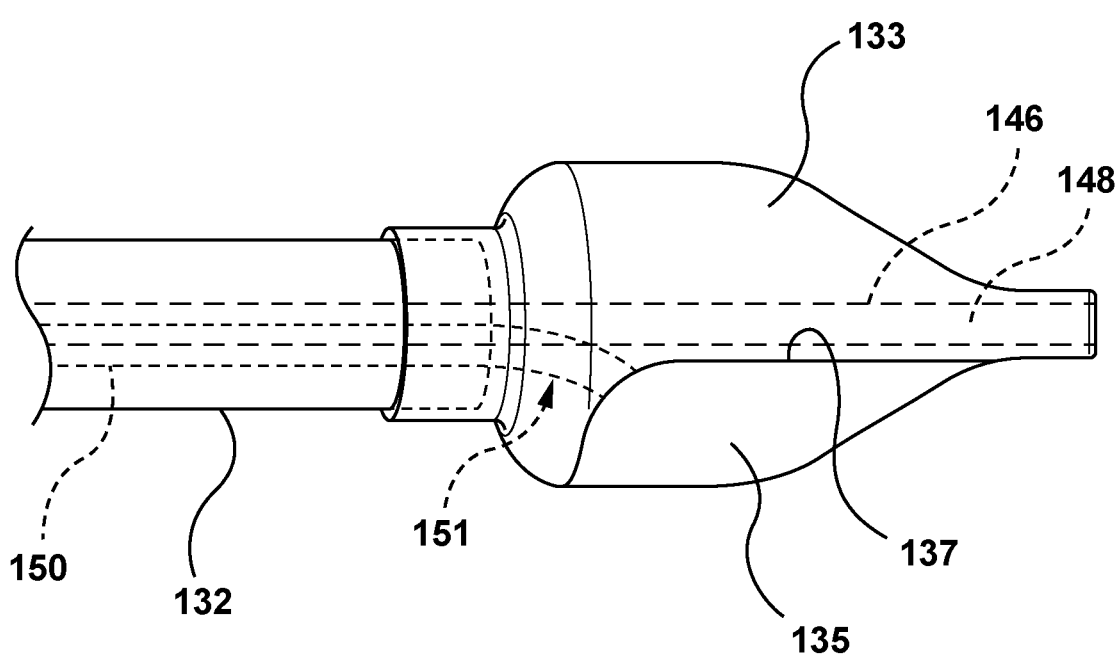
FIG. 5 is a perspective view of a nosecone of the delivery system of FIG. 1, wherein the nosecone is in the delivery configuration.
Figure 6:
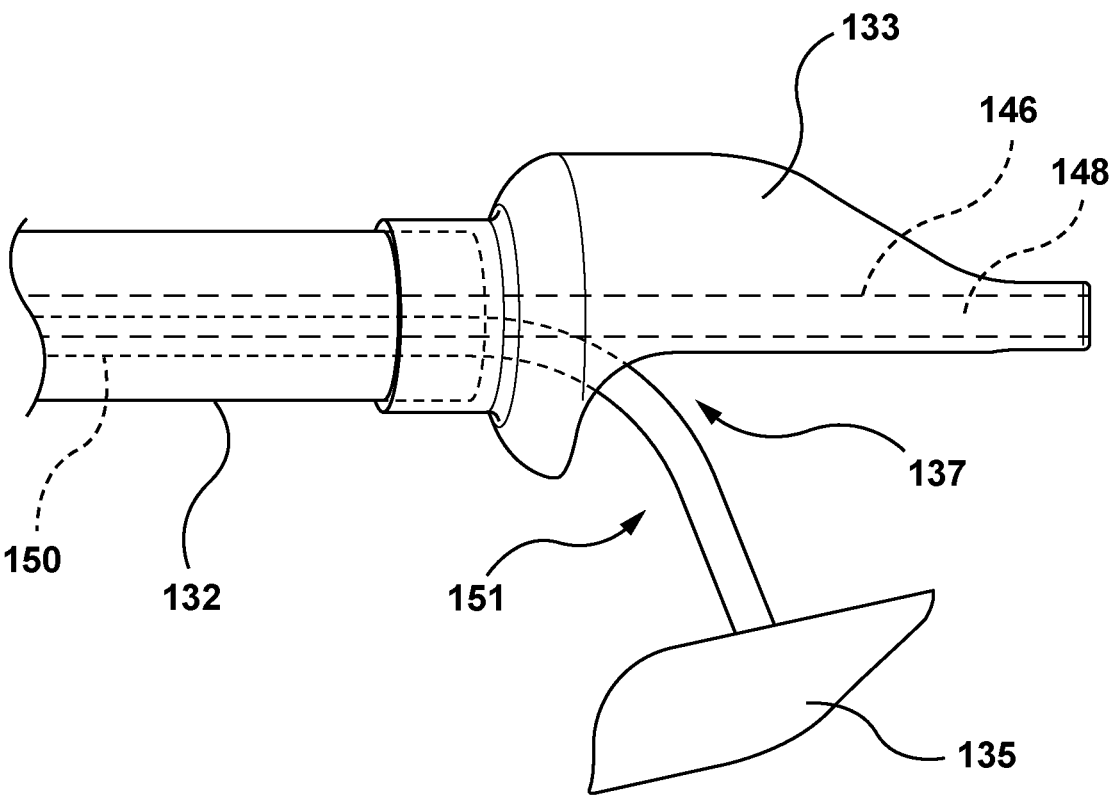
FIG. 6 is a perspective view of a nosecone of the delivery system of FIG. 1, wherein the nosecone is in a deployed configuration.

Turning now to FIGS. 5-6, the nosecone 133 of the delivery system 100 will now be described in more detail. The nosecone 133 is a split distal tip that includes the cutout portion 135 formed through a sidewall thereof such that the cutout portion 135 of the nosecone 133 may be distally advanced from the remainder of the nosecone 133 in order to contact and push against the anatomy, thereby deflecting and radially centering the heart valve prosthesis 101 disposed within the capsule 120 within the native heart valve. The push wire 150 is configured to be longitudinally translated via the first actuator 142 of the handle 140 in order to alternate the nosecone 133 between a delivery configuration and a deployed configuration. FIG. 5 is a perspective view of the nosecone 133 in the delivery configuration, while FIG. 6 is a perspective view of the nosecone 133 in the deployed configuration. The cutout portion 135 is a separable integral portion of the sidewall of the nosecone 133 that may be formed by boring, punching, piercing, or otherwise penetrating the sidewall of the nosecone 133 through the thickness of or to the interior thereof. After the cutout portion 135 is formed, the nosecone 133 includes an opening or hole 137 formed in the sidewall thereof that is configured to receive the cutout portion 135. The outer edge or perimeter of the cutout portion 135 mates with or corresponds to the interior edge of the opening 137. In an embodiment, the cutout portion 135 has the same thickness and is formed from the same material as the remaining sidewall of the nosecone 133. When the nosecone 133 is in the delivery configuration, the cutout portion 135 is positioned or received within the opening 137 and the outer surface of the cutout portion 135 is substantially flush with the outer surface of the sidewall of the nosecone 133. "Substantially flush" as used herein means that the nosecone 133 has an atraumatic or smooth profile that does not snag on the anatomy when the delivery system 100 is manipulated within the vasculature in situ.

It is not required that the cutout portion 135 has the same thickness and is formed from the same material as the remaining sidewall of the nosecone. In another embodiment, the cutout portion 135 may be formed from the same material as the remaining sidewall of the nosecone 133 but may be thicker or thinner than the remaining sidewall of the nosecone 133. Further, in another embodiment, the cutout portion 135 may be formed from a different material having the same or different thickness as the remaining sidewall of the nosecone 133. Although if formed from different materials, the materials of the nosecone 133 and the cutout portion 135 should not be so dissimilar that they come apart as the delivery device 110 is tracked over the guidewire 109.

Regardless of the material and thickness of the cutout portion 135, the cutout portion 135 is configured to be positioned or received within the opening 137 with the outer surface of the cutout portion 135 being substantially flush with the outer surface of the sidewall of the nosecone 133. Stated another way, in the delivery configuration, the cutout portion 135 sits in juxtaposition with the remaining sidewall of the nosecone 133 such that the geometry of the assembly is smooth and atraumatic.

When the nosecone is in the deployed configuration, the cutout portion 135 is no longer positioned within the opening 137 but rather is spaced apart from the opening 137 and the sidewall of the nosecone 133. More particularly, when the nosecone 133 is in the deployed configuration, the cutout portion 135 is configured to contact the anatomy of the heart. In an embodiment, the native heart valve is an aortic valve and the cutout portion 135 of the nosecone 133 is configured to contact a wall of the heart, for example, the interventricular septum. The interventricular septum is the stout wall separating the left and right ventricles of the heart from one another. The cutout portion 135 of the nosecone 133 is configured to contact and push against the interventricular septum while avoiding interference with the chordae tendineae in the left ventricle that connect to the mitral valve.

As best shown in FIG. 5, the push wire 150 includes a pre-formed bend 151 along its length, adjacent to its distal end. Due to the pre-formed bend 151 of the push wire 150, the cutout portion 135 of the nosecone 133 is directed radially outward when the push wire 150 is distally advanced in a longitudinal direction. More particularly, the pre-formed bend 151 of the push wire 150 ensures that the cutout portion 135 moves perpendicular to the central longitudinal axis LA of the delivery system 100 when the push wire 150 is pushed in a distal direction. This perpendicular movement causes an opposite, reactional movement of the remainder of the nosecone 133 when the cutout portion 135 opposes the interventricular septum. As such, when the cutout portion 135 contacts the interventricular septum in the deployed configuration, the cutout portion 135 of the nosecone 133 may be utilized to radially center the delivery system 100 within the native heart valve. More particularly, during delivery, the delivery system 100 may hug an outer edge of the aortic arch, and as a result the capsule 120 and heart valve prosthesis 101 therein may become radially offset within the native valve annulus. When the cutout portion 135 contacts the interventricular septum in the deployed configuration, the delivery system 100 having the heart valve prosthesis 101 mounted thereon is deflected and repositioned relative to the native valve annulus. The cutout portion 135 of the nosecone 133 contacts and pushes against the interventricular septum to center the capsule 120 and heart valve prosthesis 101 therein within the plane of the native valve annulus. Utilizing the nosecone 133 as a centering mechanism is particularly advantageous because the nosecone 133 is distal to the capsule 120 and is a fixed point that does not move axially or linearly during valve deployment or recapture. As such, the cutout portion 135 of the nosecone 133 may stay deployed throughout the valve deployment process without moving or changing positions in situ. After valve deployment is complete, the cutout portion 135 of the nosecone 133 may be retracted back to the delivery configuration in which the outer surface of the cutout portion 135 is substantially flush with the outer surface of the sidewall of the nosecone 133. The cutout portion 135 fits substantially back into the opening 137 such that the nosecone 133 has an atraumatic profile during removal that does not snag on the anatomy when the delivery system 100 is removed.

The push wire 150 is configured to transmit between 2 and 3 N of lateral force to the cutout portion 135 of the nosecone 133 in order to deflect the capsule 120 having the heart valve prosthesis 101 disposed therein, thereby repositioning and aligning the heart valve prosthesis 101 relative to the native valve annulus. Stated another way, the force transmitted by the push wire 150 is configured to deflect the entire distal portion of the delivery device 110, including the capsule 120 having the heart valve prosthesis 101 disposed therein, in order to reposition the heart valve prosthesis 101 prior to deployment. In an embodiment, the push wire 150 is a ribbon element having a C-shaped cross-section that provides the push wire 150 with sufficient pushability to transmit the required lateral force to deflect and reposition the heart valve prosthesis 101 relative to the native valve annulus. In another embodiment, the push wire 150 may have an alternative cross-section such as round or oval if such configurations transmit the required lateral force to deflect and reposition the heart valve prosthesis 101 relative to the native valve annulus. Further, the surface area of the cutout portion 135 of the nosecone 133 is configured to transmit the required lateral force to deflect the capsule 120 having the heart valve prosthesis 101 disposed therein while minimizing trauma to the anatomy. As such, in an embodiment, the cutout portion 135 of the nosecone 133 is at least 20% of the sidewall of the nosecone 133 such that the cutout portion 135 has a surface area that is sufficient to transmit the required lateral force to deflect and reposition the heart valve prosthesis 101 relative to the native valve annulus. In another embodiment, the cutout portion 135 of the nosecone 133 is between 20% and 45% of the sidewall of the nosecone 133.

Figures 7, 7A, 7B:
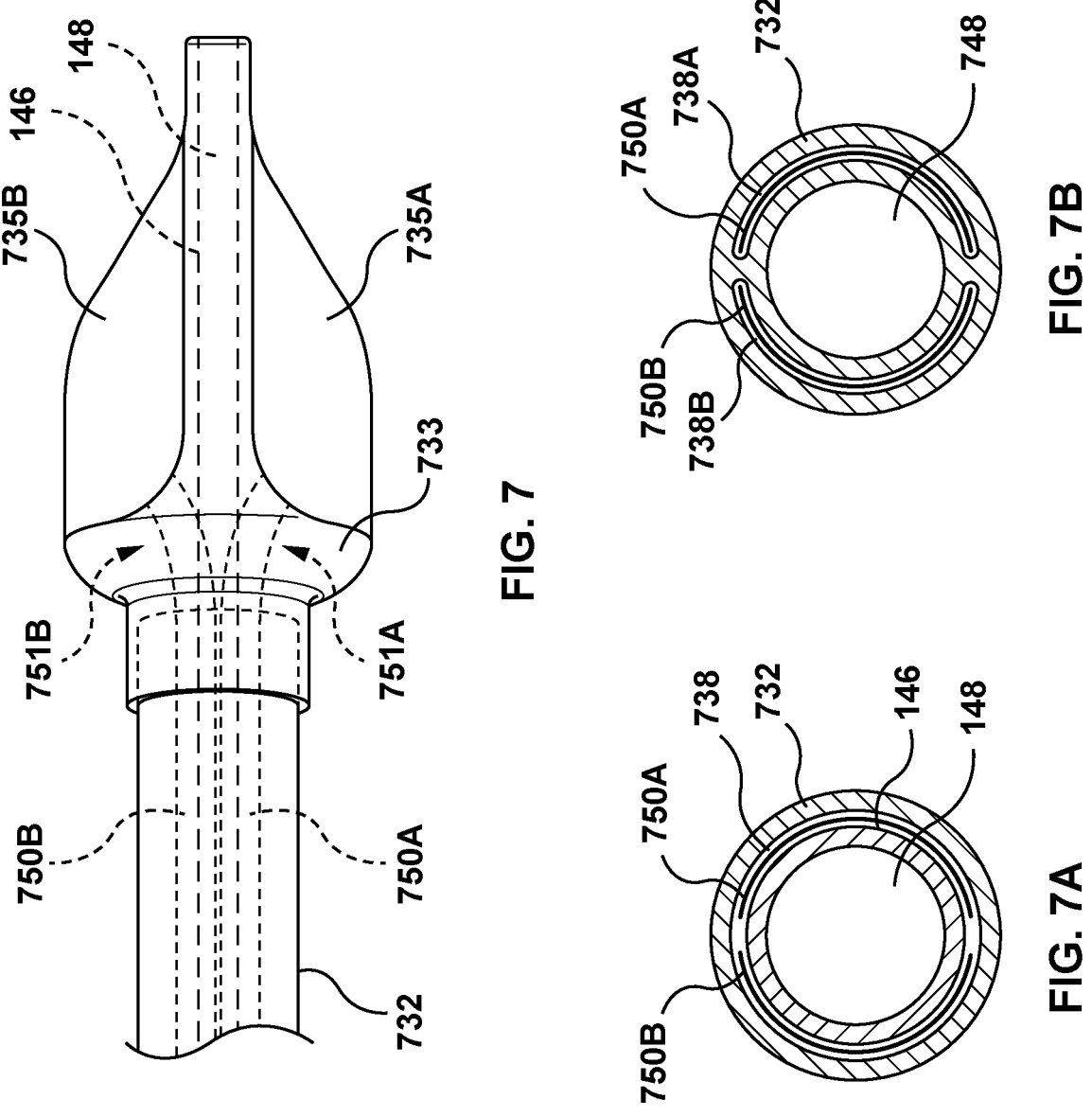
FIG. 7 is a perspective view of a nosecone of a delivery system according to another embodiment hereof, wherein the nosecone includes two cutout portions and the nosecone is in a delivery configuration.
FIG. 7A is a cross-sectional view of the delivery system of FIG. 7 taken along line A-A of FIG. 7.
FIG. 7B is a cross-sectional view of a delivery system according to another embodiment hereof taken along line A-A of FIG. 7.

When positioned in situ, the nosecone 133 as well as the outline of the native anatomy is visible to the physician under fluoroscopy and the physician may torque or rotate the delivery system 100 to properly orient the cutout portion 135 of the nosecone 133 such that the cutout portion 135 is deployed towards the interventricular septum. Further, in another embodiment, the nosecone may include multiple cutout portions integrally formed thereon to provide the physician with multiple options for deployment to ensure that one of the cutout portions of the nosecone is deployed towards the interventricular septum. Stated another way, the physician may deploy the cutout portion which is positioned or oriented towards the interventricular septum (i.e., oriented to contact the interventricular septum when deployed) without requiring the physician to torque or rotate the nosecone 133. More particularly, FIG. 7 is a perspective view of a nosecone 733 of a delivery system according to another embodiment hereof and FIG. 7A is a cross-sectional view taken along line A-A of FIG. 7. The nosecone 733 includes two cutout portions 735A, 735B that are circumferentially spaced apart around an outer surface of the nosecone 733. In an embodiment, the two cutout portions 735A, 735B are opposing such that they are formed on opposite sides of the nosecone 733.

Similar to the cutout portion 135, each of the cutout portions 735A, 735B is a separable integral portion of the sidewall of the nosecone 733 that may be formed by boring, punching, piercing, or otherwise penetrating the sidewall of the nosecone 733 through the thickness of or to the interior thereof. Each of the cutout portions 735A, 735B is formed through a sidewall of the nosecone 733. FIG. 7 illustrates the nosecone 733 in its delivery configuration in which the outer surface of each cutout portion 735A, 735B is substantially flush with the outer surface of the sidewall of the nosecone 733, but it will be understood by one of ordinary skill in the art that each of the cutout portions 735A, 735B of the nosecone 733 may be distally advanced from the remainder of the nosecone 733 into a deployed configuration in order to contact and push against the native anatomy to center the delivery system.

Each of the cutout portions 735A, 735B is attached to a respective push wire 750A, 750B, respectively. A proximal end (not shown) of the push wire 750A is operatively coupled to a dedicated actuator (not shown) of the handle (not shown) and a distal end of the push wire 750A is attached to the cutout portion 735A of the nosecone 733. The proximal end of the push wire 750A is accessible via the handle to be pulled or pushed which results in controlled longitudinal movement of the cutout portion 735A of the nosecone 733. Similarly, a proximal end (not shown) of the push wire 750B is operatively coupled to a dedicated actuator (not shown) of the handle (not shown) and a distal end of the push wire 750B is attached to the cutout portion 735B of the nosecone 733. The proximal end of the push wire 750B is accessible via the handle to be pulled or pushed which results in controlled longitudinal movement of the cutout portion 735B of the nosecone 733. Similar to the push wire 150, the push wire 750A includes a pre-formed bend 751A along its length, adjacent to its distal end, which directs the cutout portion 735A of the nosecone 733 radially outward when the push wire 750A is distally advanced in a longitudinal direction. Similarly, the push wire 750B includes a pre-formed bend 751B along its length, adjacent to its distal end, which directs the cutout portion 735B of the nosecone 733 radially outward when the push wire 750B is distally advanced in a longitudinal direction. The pre-formed bends 751A, 751A are bent or curved in opposing directions.

The nosecone 733 is attached to a distal end of an inner shaft 732. As best shown on the cross-sectional view of FIG. 7A, the inner shaft 732 defines a lumen 738 and is concentrically disposed over the guidewire shaft 146 which defines the guidewire lumen 148. Each of the push wires 750A, 750B has a C-shaped cross-section and is slidingly disposed within the lumen 738 of the inner shaft 732. Stated another way, each of the push wires 750A, 750B is slidingly disposed within the annular space defined between an inner surface of the inner shaft 732 and an outer surface of the guidewire shaft 146. In another embodiment hereof, the guidewire shaft 146 may be omitted and the inner shaft may alternatively be constructed as a triple lumen shaft formed for example by multi-lumen profile extrusion. More particularly, as shown in FIG. 7B which is a cross-sectional view of a delivery system according to another embodiment hereof taken along line A-A of FIG. 7, an inner shaft 732B defines a first or C-shaped lumen 738A which is pre-formed in the wall of the inner shaft and is configured to slidingly receive the push wire 750A having a C-shaped cross-section. The inner shaft 732B also defines a second or C-shaped lumen 738B which is pre-formed in the wall of the inner shaft and is configured to slidingly receive the push wire 750B having a C-shaped cross-section. Lastly, the inner shaft 732B also defines a third or guidewire lumen 748 configured to slidingly receive the guidewire 109 (not shown). In another embodiment (not shown), the first and second lumens 738A, 738B as well as the push wires 750A, 750B disposed there-through may have different configurations or shapes including oval or circular.

Figures 8, 9, 10:
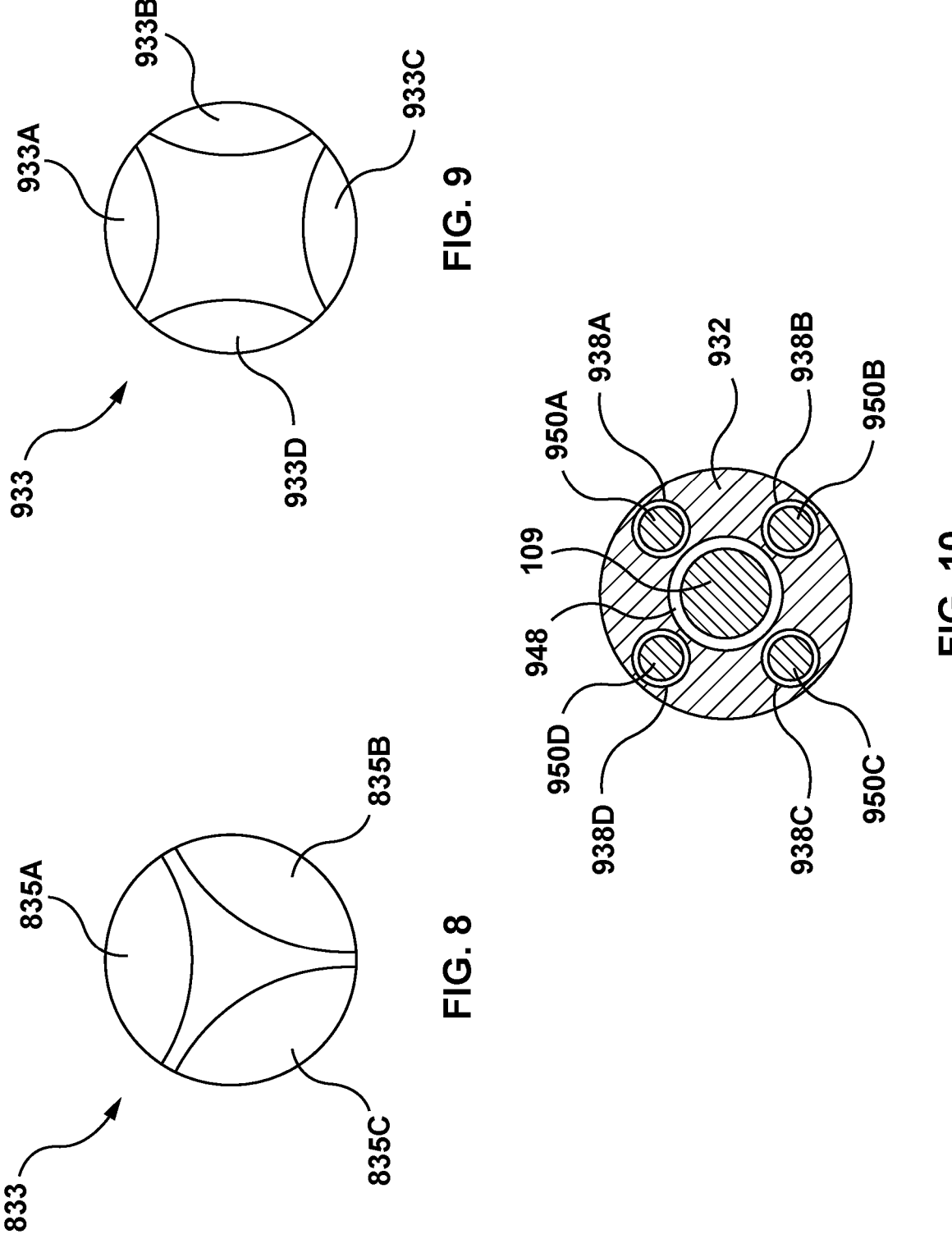
FIG. 8 is an end view of a nosecone of a delivery system according to another embodiment hereof, wherein the nosecone includes three cutout portions.
FIG. 9 is an end view of a nosecone of a delivery system according to another embodiment hereof, wherein the nosecone includes four cutout portions.
FIG. 10 is a cross-sectional view of an inner shaft of a delivery system according to another embodiment hereof, the inner shaft being removed from the delivery system for illustrative purposes only, wherein the inner shaft includes five lumens formed therethrough.

Although depicted with two integral portions in the embodiment of FIG. 7, a nosecone may have a greater number of cutout portions. For example, FIG. 8 is an end view of a nosecone 833 of a delivery system according to another embodiment hereof in which the nosecone 833 includes three cutout portions 835A, 835B, 835C that are circumferentially spaced apart around an outer surface of the nosecone 833. In another example, FIG. 9 is an end view of a nosecone 933 of a delivery system according to another embodiment hereof, wherein the nosecone includes four cutout portions 935A, 935B, 935C, 935D that are circumferentially spaced apart around an outer surface of the nosecone 933. In order to accommodate a dedicated push wire for each of the cutout portions 935A, 935B, 935C, 935D, an inner shaft 932 as shown in FIG. 10 is constructed as a multi lumen shaft formed for example by multi-lumen profile extrusion. FIG. 10 is a cross-sectional view of the inner shaft 932. More particularly, the inner shaft 932 defines a first lumen 938A which is pre-formed in the wall of the inner shaft and is configured to slidingly receive a push wire 950A having a round or circular cross-section and attached to the cutout portion 935A, a second lumen 938B which is pre-formed in the wall of the inner shaft and is configured to slidingly receive a push wire 950B having a round or circular cross-section and attached to the cutout portion 935B, a third lumen 938C which is pre-formed in the wall of the inner shaft and is configured to slidingly receive a push wire 950C having a round or circular cross-section and attached to the cutout portion 935C, and a fourth lumen 938D which is pre-formed in the wall of the inner shaft and is configured to slidingly receive a push wire 950D having a round or circular cross-section and attached to the cutout portion 935D. Lastly, the inner shaft 932 also defines a fifth or guidewire lumen 948 configured to slidingly receive the guidewire 109. Although the lumens are depicted as circular or round to accommodate a respective circular or round push wire, the lumens may be oval, rectangular, or semi-circular to accommodate a push wire of other cross-sections.

Figures 11, 12, 13:
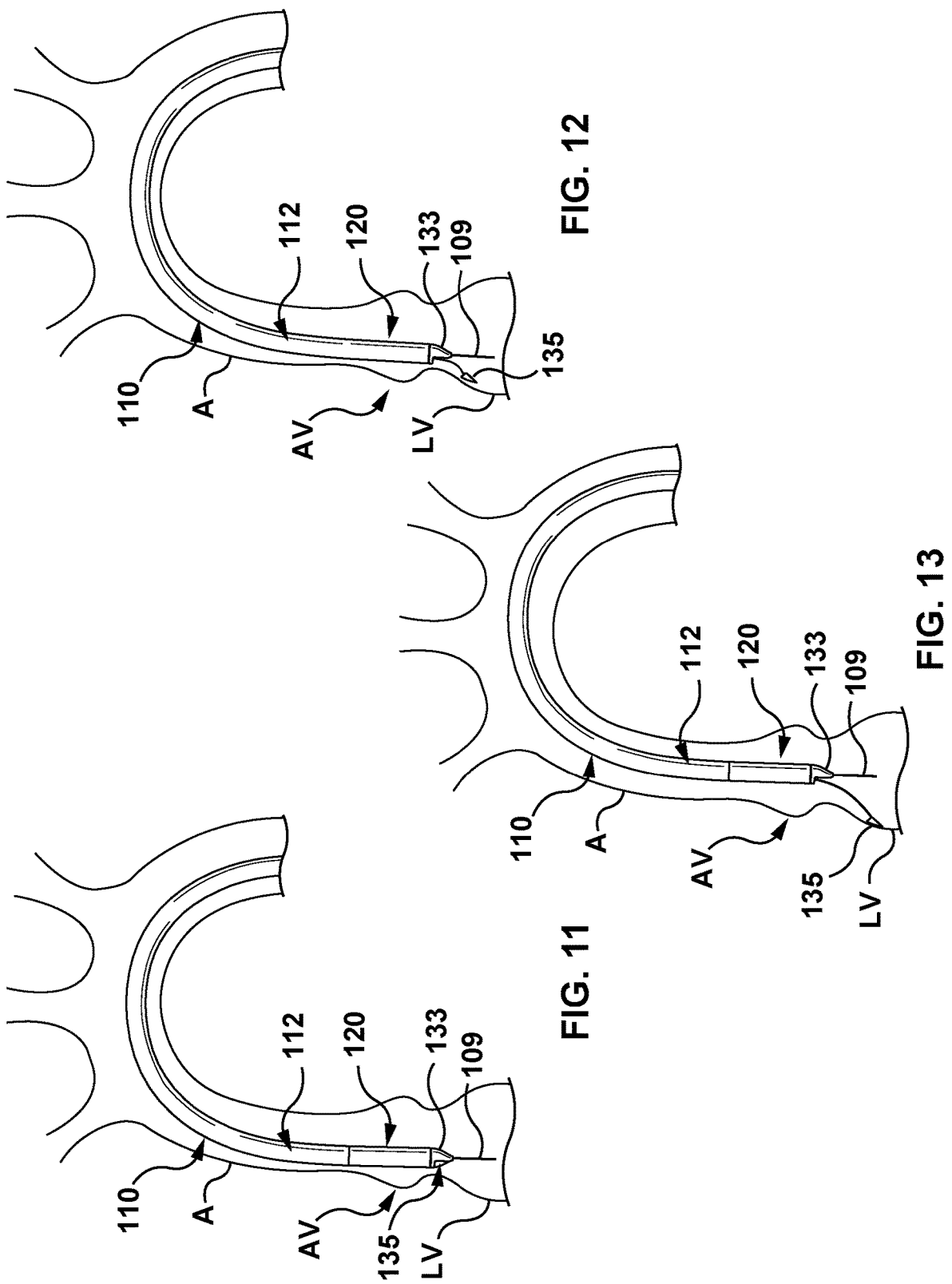
FIG. 11 illustrates a step of a method of using the delivery system of FIG. 1 to deploy the heart valve prosthesis of FIG. 3, wherein the heart valve prosthesis is shown in the delivery or radially compressed configuration at the target treatment site.
FIG. 12 illustrates another step of a method of using the delivery system of FIG. 1 to deploy the heart valve prosthesis of FIG. 3, wherein a cutout portion of the nosecone is in the process of being deployed.
FIG. 13 illustrates another step of a method of using the delivery system of FIG. 1 to deploy the heart valve prosthesis of FIG. 3, wherein a cutout portion of the nosecone contacts the interventricular septum.

A method of delivering and deploying the heart valve prosthesis 301 with the delivery device 110 is depicted in FIGS. 11-17. As shown in FIG. 11, in accordance with techniques known in the field of interventional cardiology and/or interventional radiology, the delivery system 100 including the delivery device 110 and the heart valve prosthesis 301 disposed therein is transluminally advanced in a retrograde approach through the vasculature to the treatment site, which in this instance is a target diseased native aortic valve AV that extends between a patient's left ventricle LV and a patient's aorta A. Delivery of the delivery system 100 to the native aortic valve AV is accomplished via a percutaneous retrograde transfemoral approach in which the delivery system is tracked through the femoral artery, up the aorta and around the aortic arch in order to access the native aortic valve AV. The delivery system 100 may also be positioned within the desired area of the heart via different delivery methods known in the art for accessing heart valves, for example, a retrograde method, an antegrade method, a direct or transaortic method, a subclavian artery method, a transfemoral vein or artery method, a transapical method, a transatrial method, or a transseptal method. As shown, the delivery system 100 is tracked over the guidewire 109 that has previously been inserted into the patient vasculature. During delivery, since the heart valve prosthesis 301 is self-expanding, the heart valve prosthesis 301 remains compressed within the capsule 120 of the outer sheath 112 as the delivery system 100 is manipulated and navigated through the vasculature. The delivery system 100 is advanced until the distal tip 133 thereof is distal to the native aortic valve AV and disposed within the left ventricle LV as shown in FIG. 11, such that the first end 302 of the heart valve prosthesis 301 (which is the inflow and proximal end of the heart valve prosthesis 301 when the heart valve prosthesis 301 is configured for placement in a native aortic valve) is positioned at an annulus of a native aortic heart valve. During advancement to the treatment site, the nosecone 133 is in the delivery configuration in which the cutout portion 135 thereof is substantially flush with the sidewall of the nosecone 133.

If necessary, prior to deploying the cutout portion 135, the physician may torque or rotate the delivery system 100 to orient the cutout portion 135 towards the desired heart wall, for example, the interventricular septum. FIG. 12 illustrates the cutout portion 135 of the nosecone 133 in the process of being deployed. The push wire 150 is longitudinally translated via the first actuator 142 of the handle 140 in order to distally advance the cutout portion 135 of the nosecone 133 to a deployed configuration in which the cutout portion 135 is spaced apart from the sidewall of the nosecone 133. Although FIG. 12 is shown with the nosecone 133 having a single cutout portion 135, it will be understood that if the nosecone includes multiple cutout portions such as but not limited to one of the embodiments depicted in FIG. 7, 8, or 9, the physician will choose or select to deploy one or more of the cutout portions which are positioned or oriented to contact and push against one or more walls of the heart, for example, one or more walls of the ventricle including the interventricular septum, when deployed.

As shown in FIG. 13, the cutout portion 135 of the nosecone 133 is further distally advanced or moved via the push wire 150 into contact with anatomy of the native heart valve such that the cutout portion 135 contacts and pushes against the anatomy of the native heart to radially center the distal portion of the delivery system 110, including the capsule 120 having the heart valve prosthesis 301 disposed therein, within the native heart valve. In this embodiment, the native heart valve is an aortic valve and the cutout portion 135 of the nosecone 133 contacts and pushes against the interventricular septum. The push wire 150 is configured to transmit between 2 and 3 N of lateral force to the cutout portion 135 of the nosecone 133 in order to deflect and reposition the heart valve prosthesis 301 relative to the native valve annulus. More particularly, when the cutout portion 135 contacts the interventricular septum in the deployed configuration, the delivery system 100 having the heart valve prosthesis 301 mounted thereon is deflected and repositioned relative to the native valve annulus. The cutout portion 135 of the nosecone 133 contacts and pushes against the interventricular septum to deflect the capsule 120 and heart valve prosthesis 301 therein in order to radially center the heart valve prosthesis within the native heart valve.

Figure 14:
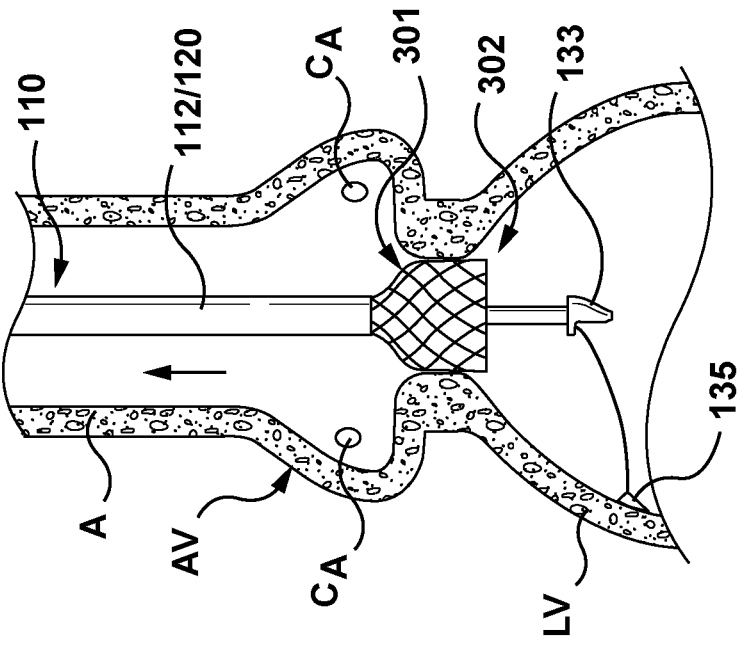
FIG. 14 illustrates another step of a method of using the delivery system of FIG. 1 to deploy the heart valve prosthesis of FIG. 3, wherein the heart valve prosthesis is shown being transitioned from the delivery or radially compressed configuration to the deployed or radially expanded configuration at the target treatment site and wherein a cutout portion of the nosecone contacts the interventricular septum.

After the capsule 120 and heart valve prosthesis 301 are centered within the native valve annulus, the heart valve prosthesis 301 is deployed at the annulus of the native aortic heart valve AV as shown in FIG. 14, which is a sectional view of the native aortic heart valve AV. During deployment of the heart valve prosthesis 301, the outer sheath 112 (and the capsule 120 forming the distal portion of the outer sheath 112) is proximally retracted. FIG. 14 illustrates the heart valve prosthesis 301 being transitioned from the delivery or radially compressed configuration to the deployed or radially expanded configuration. Notably, the nosecone 133 remains in the deployed configuration while the heart valve prosthesis 301 is deployed. The nosecone 133 is distal to the capsule 120 and is a fixed point that does not move axially or linearly during valve deployment or recapture. As such, the cutout portion 135 of the nosecone 133 may stay deployed throughout the valve deployment process.

At this stage of deployment, positioning of the delivery system 100 may still be adjusted and/or the outer sheath 112 and the capsule 120 may be distally advanced to recapture the heart valve prosthesis 301. For example, in an embodiment, the outer sheath 112 and the capsule 120 may be distally advanced to recapture the heart valve prosthesis 301 until a predetermined length of the heart valve prosthesis 301 is exposed, for example, until approximately two-thirds of the length of the heart valve prosthesis 301 is exposed. If it is determined that the rotational position of the heart valve prosthesis 301 is not optimal after retraction of the outer sheath 112 and the capsule 120 has been initiated, the user may recapture the heart valve prosthesis 301, retract the cutout portion 135 of the nosecone, and reposition the delivery system 100 by pushing, pulling and/or torqueing the delivery device 110. Once positioned as desired, the cutout portion 135 may be re-deployed and deployment of the heart valve prosthesis 301 may be attempted again.

Figure 15:
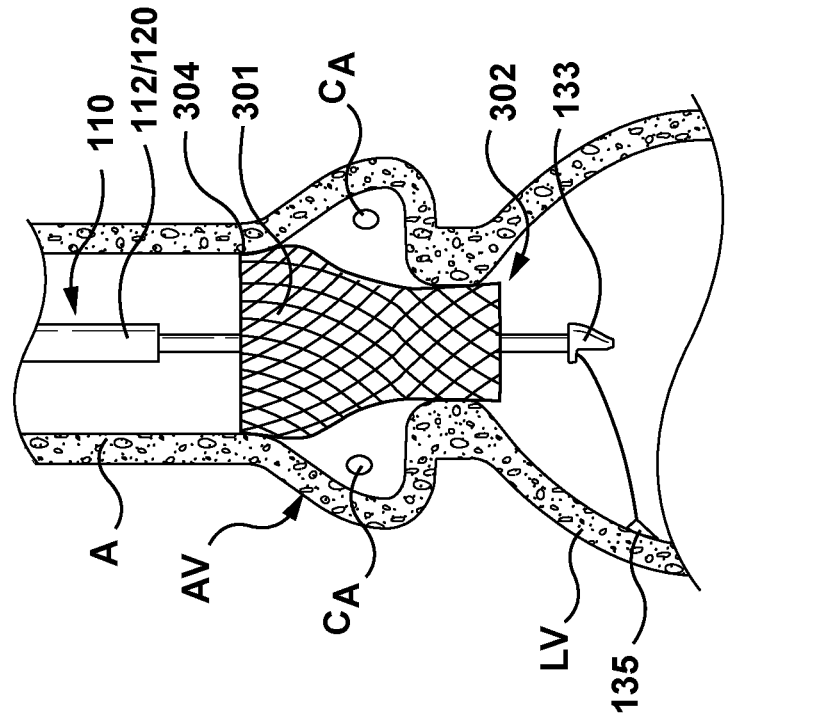
FIG. 15 illustrates another step of a method of using the delivery system of FIG. 1 to deploy the heart valve prosthesis of FIG. 3, wherein the heart valve prosthesis is shown in the deployed or radially expanded configuration at the target treatment site and wherein a cutout portion of the nosecone contacts the interventricular septum.

When the outer sheath 112 is retracted such that all of the heart valve prosthesis 301 is uncovered, the heart valve prosthesis 301 is released from the prosthesis retention member of the delivery system 100, for example, by being released from the spindle 108 on the distal end 126 of the middle shaft 122. FIG. 15 illustrates the heart valve prosthesis 301 in the fully deployed or radially expanded configuration at the target treatment site, with the nosecone 133 still in the deployed configured.

Figure 17:
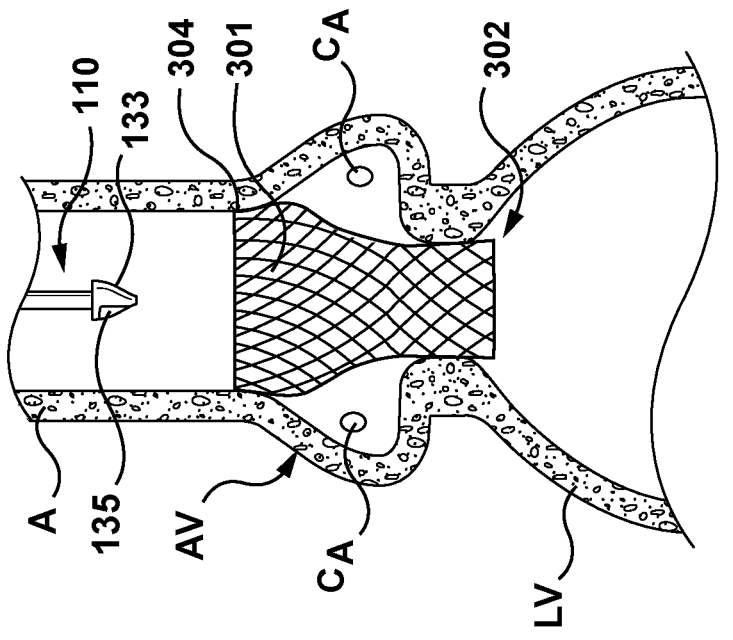
FIG. 17 illustrates another step of a method of using the delivery system of FIG. 1 to deploy the heart valve prosthesis of FIG. 3, wherein the heart valve prosthesis is shown in the deployed or radially expanded configuration following deployment at the target treatment site and the delivery system is being removed.
Figure 16:
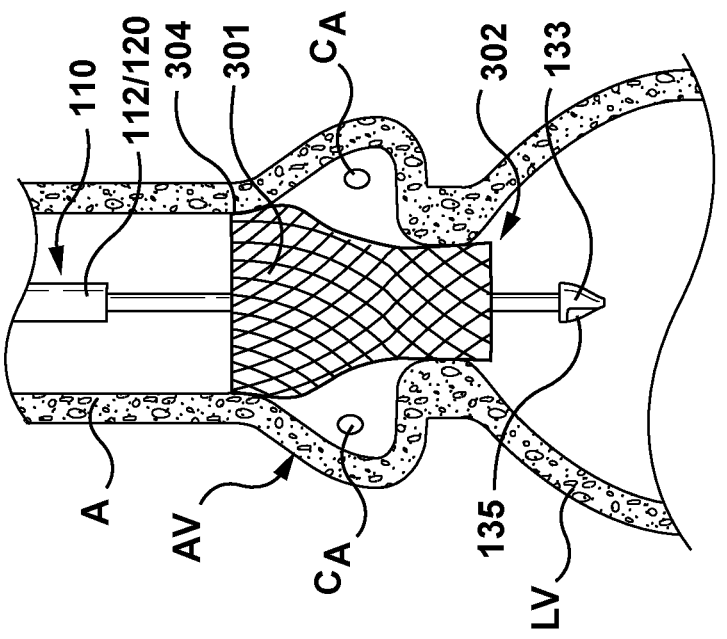
FIG. 16 illustrates another step of a method of using the delivery system of FIG. 1 to deploy the heart valve prosthesis of FIG. 3, wherein the heart valve prosthesis is shown in the deployed or radially expanded configuration at the target treatment site and wherein a cutout portion of the nosecone is repositioned back to the delivery configuration.

After valve deployment is complete, the cutout portion 135 of the nosecone 133 is repositioned or retracted back to the delivery configuration in which the outer surface of the cutout portion 135 is substantially flush with the outer surface of the sidewall of the nosecone 133 as shown in FIG. 16. The nosecone 133 is repositioned back to the delivery configuration by longitudinally retracting the push wire 150. The cutout portion 135 fits substantially back into the opening 137 such that the nosecone 133 has an atraumatic profile during removal that does not snag on the anatomy when the delivery system 100 is removed. As shown in FIG. 17, after deployment of the heart valve prosthesis 301 is complete and the nosecone 133 is returned to its delivery configuration, the delivery device 110 is then removed and the heart valve prosthesis 301 remains deployed within the native target heart valve.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A delivery system for percutaneously delivering a heart valve prosthesis to a native heart valve, the delivery system comprising:
    a handle having at least one actuator thereon;
    an inner shaft having a distal portion configured to receive the heart valve prosthesis thereon, the inner shaft defining at least one lumen therethrough and including a nosecone attached to a distal end thereof, wherein the nosecone includes at least one cutout portion formed through a sidewall thereof; and at least one push wire slidingly disposed through the at least one lumen of the inner shaft, wherein a proximal end of the at least one push wire is operatively coupled to the at least one actuator of the handle and a distal end of the at least one push wire is attached to the at least one cutout portion of the nosecone;

wherein when the nosecone is in a delivery configuration the at least one cutout portion is substantially flush with the sidewall of the nosecone and when the nosecone is in a deployed configuration the at least one cutout portion is spaced apart from the sidewall of the nosecone.

2. The delivery system of claim 1, wherein the at least one push wire includes a pre-formed bend adjacent to the distal end thereof and is configured to be longitudinally translated in order to alternate the nosecone between the delivery configuration and the deployed configuration.

3. The delivery system of claim 1, further comprising an outer sheath configured to cover the heart valve prosthesis during delivery, wherein the inner shaft is disposed within the outer sheath and the outer sheath is retractable relative to the inner shaft.

4. The delivery system of claim 3, further comprising a middle shaft slidingly disposed between the outer sheath and the inner shaft, wherein a distal end of the middle shaft is configured to releasably attach to the heart valve prosthesis.

5. The delivery system of claim 3, wherein the heart valve prosthesis is self-expanding and a distal portion of the outer sheath includes a capsule configured to compressively retain the heart valve prosthesis during delivery.

6. The delivery system of claim 3, wherein the outer sheath includes a proximal end operatively coupled to the handle and a distal portion that is configured to cover the heart valve prosthesis during delivery, and wherein the handle includes a first actuator and a second actuator, the first actuator being configured to longitudinally move the at least one push wire and the second actuator being configured to proximally retract the outer sheath.

7. The delivery system of claim 1, wherein the at least one lumen of the inner shaft includes a first lumen and a second lumen, the at least one push wire being slidingly disposed through the first lumen and the second lumen being configured to slidingly receive a guidewire.

8. The delivery system of claim 1, wherein the at least one cutout portion of the nosecone is configured to contact and push against the anatomy of the native heart valve and radially center the delivery system within the native heart valve.

9. The delivery system of claim 8, wherein the native heart valve is an aortic valve and the at least one cutout portion of the nosecone is configured to contact the interventricular septum.

10. The delivery system of claim 9, wherein the at least one push wire is configured to transmit between 2 and 3 N of lateral force to radially center the delivery system within the native heart valve.

11. The delivery system of claim 1, wherein the at least one cutout portion of the nosecone is at least 20% of the sidewall of the nosecone.

12. The delivery system of claim 1, wherein the at least one cutout portion includes a plurality of cutout portions, the plurality of cutout portions being circumferentially spaced apart around an outer surface of the nosecone, and wherein the at least one push wire includes a plurality of push wires, with a push wire of the plurality of push wires being attached to a respective cutout portion of the plurality of cutout portions.

13. The delivery system of claim 1, wherein when the nosecone is in the delivery configuration the at least one cutout portion is disposed within an opening formed within the sidewall of the nosecone and when the nosecone is in the deployed configuration the at least one cutout portion is spaced apart from the opening formed within the sidewall of the nosecone.

\* \* \* \* \*